(12) United States Patent
Gielen et al.

(10) Patent No.: US 9,249,435 B2
(45) Date of Patent: Feb. 2, 2016

(54) PROCESS FOR THE IMPROVED SEPARATION OF A HYDROPHOBIC ORGANIC SOLUTION FROM AN AQUEOUS CULTURE MEDIUM

(71) Applicants: Jasmin Gielen, Bochum (DE); Thomas Haas, Muenster (DE); Hans-Georg Hennemann, Marl (DE); Steffen Schaffer, Herten (DE); Mirja Wessel, Bochum (DE); Katharina Berse, Waltrop (DE); Marion Schiebelhut, Haltern (DE); Sabine Hafkemeyer, Marl (DE); Markus Poetter, Muenster (DE); Frank Erhardt, Bielefeld (DE)

(72) Inventors: Jasmin Gielen, Bochum (DE); Thomas Haas, Muenster (DE); Hans-Georg Hennemann, Marl (DE); Steffen Schaffer, Herten (DE); Mirja Wessel, Bochum (DE); Katharina Berse, Waltrop (DE); Marion Schiebelhut, Haltern (DE); Sabine Hafkemeyer, Marl (DE); Markus Poetter, Muenster (DE); Frank Erhardt, Bielefeld (DE)

(73) Assignee: EVONIK DEGUSSA GmbH, Essen (DE)

(*) Notice: Subject to any disclaimer, the term of this patent is extended or adjusted under 35 U.S.C. 154(b) by 130 days.

(21) Appl. No.: 13/721,481

(22) Filed: Dec. 20, 2012

(65) Prior Publication Data

US 2013/0164797 A1 Jun. 27, 2013

(30) Foreign Application Priority Data

Dec. 22, 2011 (EP) .................................... 11195221

(51) Int. Cl.
  *C12P 13/04* (2006.01)
  *C12P 7/64* (2006.01)
  *C12N 9/02* (2006.01)

(52) U.S. Cl.
  CPC ............... *C12P 7/6436* (2013.01); *C12N 9/001* (2013.01); *C12P 13/04* (2013.01); *C12Y 103/99003* (2013.01)

(58) Field of Classification Search
  None
  See application file for complete search history.

(56) References Cited

U.S. PATENT DOCUMENTS

| | | | |
|---|---|---|---|
| 6,620,970 B2 | 9/2003 | Schiffer et al. | |
| 6,639,108 B2 | 10/2003 | Schiffer et al. | |
| 6,861,540 B2 | 3/2005 | Herwig et al. | |
| 6,878,836 B2 | 4/2005 | Haas et al. | |
| 7,030,052 B2 | 4/2006 | Stochniol et al. | |
| 7,049,450 B2 | 5/2006 | Hofen et al. | |
| 7,091,384 B2 | 8/2006 | Jaeger et al. | |
| 7,507,862 B2 | 3/2009 | Stochniol et al. | |
| 7,879,938 B2 | 2/2011 | Häger et al. | |
| 7,923,225 B2 | 4/2011 | Mueller et al. | |
| 8,349,596 B2 | 1/2013 | Mueller et al. | |
| 8,399,658 B2 | 3/2013 | Hengstermann et al. | |
| 8,445,720 B2 | 5/2013 | Hannen et al. | |
| 8,703,451 B2 | 4/2014 | Haas et al. | |
| 8,703,993 B2 | 4/2014 | Hannen et al. | |
| 8,809,576 B2 | 8/2014 | Schraven et al. | |
| 9,000,223 B2 | 4/2015 | Micoine et al. | |
| 2002/0087036 A1 | 7/2002 | Haas et al. | |
| 2010/0071259 A1 | 3/2010 | Hu et al. | |
| 2010/0190219 A1 | 7/2010 | Schaffer et al. | |
| 2010/0261237 A1 | 10/2010 | Verseck et al. | |
| 2010/0266518 A1 | 10/2010 | Springer et al. | |
| 2010/0291644 A1 | 11/2010 | Marx et al. | |
| 2010/0324257 A1 | 12/2010 | Karau et al. | |
| 2011/0118433 A1 | 5/2011 | Pötter et al. | |
| 2011/0118504 A1 | 5/2011 | Haas et al. | |
| 2011/0171702 A1 | 7/2011 | Reinecke et al. | |
| 2011/0251399 A1 | 10/2011 | Dingerdissen et al. | |
| 2011/0269977 A1 | 11/2011 | Dingerdissen et al. | |
| 2012/0034665 A1 | 2/2012 | Haas et al. | |
| 2012/0041216 A1 | 2/2012 | Sieber et al. | |
| 2012/0315366 A1 | 12/2012 | Zehnacker et al. | |
| 2013/0165685 A1 | 6/2013 | Hannen et al. | |
| 2013/0183725 A1 | 7/2013 | Poetter et al. | |

(Continued)

FOREIGN PATENT DOCUMENTS

WO WO 2008/148640 A1 12/2008
WO WO 2009/077461 A1 6/2009

(Continued)

OTHER PUBLICATIONS

Kalscheuer et al. "Microdiesel: *Escherichia coli* engineered for fuel production" Microbiology 2006 152 2529-2536.*

(Continued)

*Primary Examiner* — Suzanne M Noakes
(74) *Attorney, Agent, or Firm* — Oblon, McClelland, Maier & Neustadt, L.L.P.

(57) ABSTRACT

A process for the improved separation of a hydrophobic organic solution from an aqueous culture medium is provided. The process includes preparing an aqueous culture medium of a metabolically active cell having a decreased activity; contacting of the aqueous culture medium with a hydrophobic organic solution comprising a substrate for biotransformation; conducting a biotransformation of the substrate; and separating the hydrophobic organic solution comprising a biotransformed substrate from the aqueous culture medium. The decreased activity of the metabolically active cell is in comparison to a wild-type of the active cell and the decreased activity is of at least of one enzyme that catalyzes one reaction of β-oxidation of fatty acids. The invention further provides a metabolically active cell that has a decreased activity, compared to its wild-type, of an enzyme that catalyzes one of the reactions of the β-oxidation of fatty acids, including an enzyme selected from FadA, FadB, FadD, FadL and FadE as well as variants thereof.

13 Claims, 9 Drawing Sheets

(56) References Cited

U.S. PATENT DOCUMENTS

| | | |
|---|---|---|
| 2014/0039210 A1 | 2/2014 | Erhardt et al. |
| 2014/0054224 A1 | 2/2014 | Erhardt et al. |
| 2014/0120587 A1 | 5/2014 | Haas et al. |
| 2014/0141478 A1 | 5/2014 | Schaffer et al. |
| 2014/0178948 A1 | 6/2014 | Schaffer et al. |
| 2014/0186905 A1 | 7/2014 | Schaffer et al. |
| 2014/0242646 A1 | 8/2014 | Poetter et al. |
| 2014/0256904 A1 | 9/2014 | Schaffer et al. |
| 2014/0308717 A1 | 10/2014 | Haas et al. |

FOREIGN PATENT DOCUMENTS

| | | |
|---|---|---|
| WO | WO 2010/021711 A1 | 2/2010 |
| WO | WO 2011/131420 A1 | 10/2011 |
| WO | WO 2011/157496 A1 | 12/2011 |
| WO | WO 2011/157573 A2 | 12/2011 |
| WO | WO 2012/139666 A1 | 10/2012 |

OTHER PUBLICATIONS

U.S. Appl. No. 13/642,412, filed Oct. 19, 2012, Poetter, et al.
European Search Report Issued Jan. 25, 2013 in Patent Application No. 12197644.3 (with English translation).
Yangkai Duan et al., "*De novo* Biosynthesis of Biodiesel by *Escherichia coli* in Optimized Fed-Batch Cultivation", PLOS One, XP055026594, vol. 6, Issue 5, May 2011, pp. 1-7.
Eric J. Steen et al., "Microbial production of fatty-acid-derived fuels and chemicals from plant biomass", Nature, XP055011271, vol. 463, Jan. 2010, pp. 559-563.
U.S. Appl. No. 14/110,450, filed Oct. 8, 2013, Klasovsky, et al.
U.S. Appl. No. 14/435,339, filed Apr. 13, 2015, Engel, et al.
U.S. Appl. No. 14/419,580, filed Feb. 4, 2015, Erhardt, et al.
U.S. Appl. No. 14/425,180, filed Mar. 2, 2015, Ortelt, et al.
U.S. Appl. No. 14/363,178, filed Jun. 5, 2014, Haas et al.
U.S. Appl. No. 14/390,133, filed Oct. 2, 2014, Hennemann et al.
U.S. Appl. No. 14/400,379, filed Nov. 11, 2014, Haas et al.
U.S. Appl. No. 14/380,483, filed Aug. 22, 2014, Schiemann et al.
U.S. Appl. No. 14/363,165, filed Jun. 5, 2014, Pfeffer et al.
U.S. Appl. No. 14/367,610, filed Jun. 20, 2014, Haas et al.
U.S. Appl. No. 14/373,089, filed Jul. 18, 2014, Engel et al.
U.S. Appl. No. 14/384,301, filed Sep. 10, 2014, Schaffer et al.
U.S. Appl. No. 14/395,666, filed Oct. 20, 2014, Haas et al.
U.S. Appl. No. 14/405,050, filed Dec. 2, 2014, Haas et al.

\* cited by examiner

PROCESS FOR THE IMPROVED SEPARATION OF A HYDROPHOBIC ORGANIC SOLUTION FROM AN AQUEOUS CULTURE MEDIUM

CROSS REFERENCE TO RELATED APPLICATIONS

This application claims priority to EP 11195221, filed Dec. 22, 2011, the disclosure of which is incorporated herein by reference in its entirety.

BACKGROUND OF THE INVENTION

The present application relates to a process for the improved separation of a hydrophobic organic solution from an aqueous culture medium comprising the steps, provision of an aqueous culture medium comprising a metabolically active cell, contacting of the aqueous culture medium with a hydrophobic organic solution, separation of the hydrophobic organic solution from the aqueous culture medium, the cell having a decreased activity, compared to its wild-type, at least of one enzyme that catalyses one of the reactions of the β-oxidation of fatty acids. The invention furthermore relates to the use of a metabolically active cell that has a decreased activity, compared to its wild-type, of an enzyme that catalyses one of the reactions of the β-oxidation of fatty acids, preferably of an enzyme selected from the group comprising FadA, FadB, FadD, FadL and FadE as well as variants thereof, more preferably FadE, for the improved separation of a hydrophobic organic solution from an aqueous culture medium comprising the metabolically active cell.

A fundamental problem in processes for the production of fine chemicals starting from renewable raw materials instead of fossil fuels consists in converting the product once obtained, which is typically initially present in a large-volume aqueous phase, to a hydrophobic organic phase. This conversion is necessary on the one hand to concentrate a finished intermediate or final product and optionally to make possible the synthetic processing in the following reaction steps in organic solution, and on the other hand to improve the yield of the reaction in the aqueous phase by the removal of the desired product or firstly to make possible the course of the reaction in a technically meaningful context at all, in particular when the presence of the product acts disadvantageously on the reaction progress on account of toxicity to the production strain or an inhibition of a relevant biocatalyst by the product. The direct thermal concentration of the product, frequently present in low concentrations, from the large-volume aqueous solution is generally not expedient.

An example of such a strongly demanded product industrially, which is conventionally produced starting from hydrocarbons contained in petroleum, is 12-aminolauric acid (ALA) or its methyl ester (ALAME). ALA is an important starting product in the production of polymers, for example for the production of piping systems based on Nylon. Conventionally, ALA is produced in low yield starting from fossil raw materials in a process via laurolactam, which is synthesized by trimerization of butadiene, subsequent hydrogenation with formation of cyclododecane, subsequent oxidation to cyclododecanone, reaction with hydroxylamine and subsequent Beckmann rearrangement. A promising new route to the biotechnological production of ALA or ALAME is described in WO 2009/077461. The biotechnological process on which this route is based may be conducted in a two-phase system using a liquid ion exchanger, as is described in EP 11154707.

The workup of a product from an aqueous phase by means of an extraction into a hydrophobic organic phase firstly requires that this product has an adequate tendency to enter into the organic phase in a two-phase system comprising an aqueous, hydrophilic phase and an organic, hydrophobic phase that do not mix, which depends significantly on the physicochemical properties of the respective compound. While compounds with a high content of or consisting exclusively of unsubstituted hydrocarbons enrich mainly in the hydrophobic phase, compounds with a high content of polar groups such as heteroatom-containing functionalities and very particularly compounds with charges are mainly or virtually exclusively present in the aqueous phase, which complicates a transfer to an organic phase.

The partition of a compound in the two-phase system mentioned after adjustment of equilibrium is frequently described with the aid of partition coefficients, for example according to Nernst's equation $$\alpha = c_{phase\ 1}/c_{phase\ 2}.$$

A special partition coefficient is $K_{ow}$, also described as the P value, which characterizes the partition equilibrium of a compound between an octanol and an aqueous phase:

$$K_{ow} = P = c_{octanol}/c_{water}$$

A further prerequisite for the workup of the product from the hydrophobic phase consists in that the partition has reached the equilibrium state, which is described by the aforementioned equations, or at least approaches it sufficiently. The adjustment of the equilibrium is determined, inter alia, by the size of the contact area between both phases, a factor that is generally non-limiting in the case of biotechnological processes, since the contact area is already increased by measures such as aeration and the thorough stirring of the aqueous culture medium and the hydrophobic organic solution, which are necessary anyway due to maintenance of high densities of metabolically active cells.

Before such a reaction mixture, in which the hydrophobic organic solution is mainly present in micelles or other subcompartments, can be worked up efficiently, however, a separation of the two phases is necessary. The formation of two phases often takes place spontaneously and without any further action on mixing pure water with a pure organic hydrophobic solvent. However, the separation of an organic hydrophobic solution from a complex aqueous culture medium is less simple because of the many possible component interactions and without technical support, for example centrifugation, the separation may require from several hours to several days.

For the large-scale production of industrially demanded chemical compounds by of biotechnological processes, the process of phase separation may be a factor of considerable importance in the development and application of processes for resource-saving and rapid production and workup of compounds such as ALA. If the product is removed dissolved in a hydrophobic organic solution from a large-volume aqueous phase in a large reactor and subsequently processed, in addition to the parameters relevant for the actual production, such as type and amount of substrates, temperature and oxygen content of the medium, the separation of the hydrophobic solution must be optimized to save resources and to make the entire process as environmentally friendly as possible. Since numerous hydrophobic organic solvents used on a large scale may have a toxic action on organisms used biotechnologically, at least on relatively long contact, it is desirable to shorten the contact between the organism in the aqueous culture medium. By minimizing such contact with solvents, the protection biotechnologically used strains may be protected and release of undesired by-products released during the lysis of cells contaminating or even decomposing the target product may be prevented.

SUMMARY OF THE INVENTION

Therefore, an object of the present invention is to provide a process for the improved preparation and production of biotechnologically produced products in a biphasic system comprising an aqueous culture medium using a metabolically active cell and a hydrophobic organic solution. In particular, the object is to improve the separation of the hydrophobic organic solution and the extraction of a biotechnologically produced product soluble therein with respect to the rapidity of the process and/or the extent of the separation of the hydrophobic organic solution from the aqueous culture medium in a given time window.

A further object of the invention is to provide a biotechnologically usable cell with high resistance against the toxicity of hydrophobic phase separation solutions.

Additionally, an object of the present invention is to provide a biotechnological process for the production of hydrophobic compounds, in which oxygen consumption is reduced, and a cell suitable for this purpose.

These and further objects are achieved by the present application, the first embodiment of which includes an enzymatic two-phase system process, comprising:

preparing an aqueous culture medium of a metabolically active cell having a decreased activity;

contacting of the aqueous culture medium with a hydrophobic organic solution comprising a substrate for biotransformation;

conducting a biotransformation of the substrate; and separating the hydrophobic organic solution comprising a biotransformed substrate from the aqueous culture medium;
wherein
the decreased activity of the metabolically active cell is in comparison to a wild-type of the active cell,
and the decreased activity is of at least of one enzyme that catalyses one reaction of β-oxidation of fatty acids.

In a preferred embodiment, the at least one enzyme having decreased activity is selected from the group consisting of FadA, FadB, FadD, FadE and FadL and variants thereof. Most preferably, the enzyme is FadE or a variant thereof.

In another embodiment the present invention provides a method for separating a hydrophobic organic solution from an aqueous culture medium comprising a metabolically active cell, the method comprising: catalysing the metabolic activity with an active cell that has a decreased activity of an enzyme that catalyses a reaction of the β-oxidation of fatty acids, compared to the activity of a wild-type of the active cell.

In a further embodiment, the present invention provides a method for separating a hydrophobic organic solution from an aqueous culture medium comprising a metabolically active cell, the method comprising: catalysing the metabolic activity with a knockout of an enzyme that catalyses one reaction of the β-oxidation of fatty acids, as part of a genetic make-up of the metabolically active.

The present invention also provides a cell, comprising: an enzyme of the β-oxidation of fatty acids having a decreased activity, compared to a wild-type of the cell; wherein the cell further comprises a recombinant monooxygenase.

DETAILED DESCRIPTION OF THE INVENTION

Figure 1:
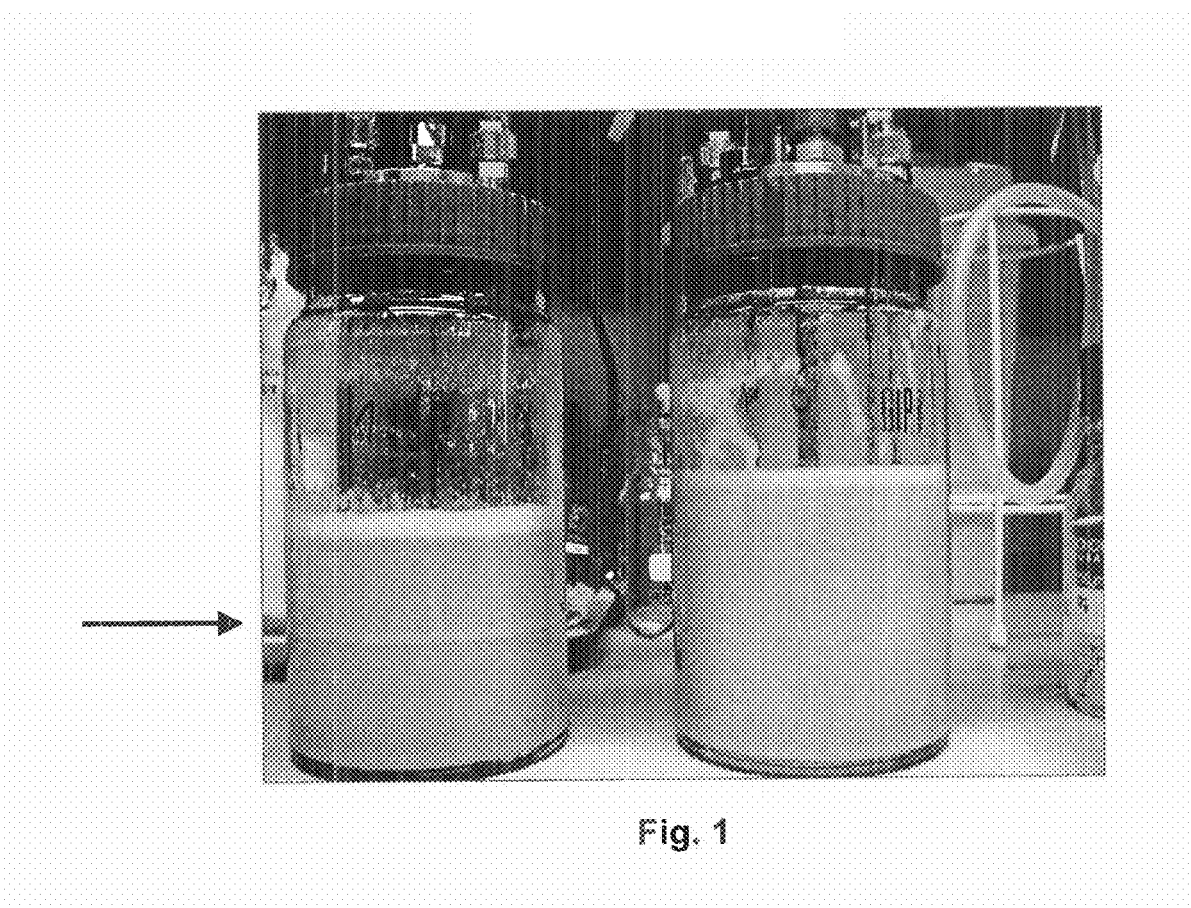
FIG. 1 shows an example of phase separation according to the invention in comparison to two phase mixture not according to the invention.

In the first embodiment, the present invention provides an enzymatic two-phase system process, comprising:

preparing an aqueous culture medium of a metabolically active cell having a decreased activity;

contacting of the aqueous culture medium with a hydrophobic organic solution comprising a substrate for biotransformation;

conducting a biotransformation of the substrate; and separating the hydrophobic organic solution comprising a biotransformed substrate from the aqueous culture medium;
wherein
the decreased activity of the metabolically active cell is in comparison to a wild-type of the active cell,
and the decreased activity is of at least of one enzyme that catalyses one reaction of β-oxidation of fatty acids.

The inventors of the present invention have discovered that a hydrophobic organic solution may surprisingly be separated off from an aqueous culture medium comprising a metabolically active cell if the metabolically active cell has a decreased activity of at least of one enzyme that catalyses one of the reactions of the β-oxidation of fatty acids, compared to its wild-type.

Furthermore, the inventors of the present invention have surprisingly discovered that a metabolically active cell that has a decreased activity of at least one enzyme that catalyses one of the reactions of the β-oxidation of fatty acids has a lower oxygen demand and a higher ratio of product yield to oxygen consumption in a biotechnological process compared to its wild-type with comparable production capacity with respect to the target product.

Without wanting to be bound to any theory, the inventors suggest that the decreased activity of at least one of enzyme that catalyses one of the reactions of the β-oxidation leads to a decrease in the concentration of hitherto unidentified metabolites, that act as detergents, in the aqueous culture medium, such that on the one hand the contact area between the hydrophobic solution and the solvent-sensitive metabolically active cells found in the aqueous culture medium is decreased on culturing cells with stirring of the medium. This decrease may lead to a reduction of the solvent stress for the cells, and on the other hand the formation of separate phases may be promoted after switching off the stirring apparatus.

The method according to the invention may be used for improving all biotechnological processes that comprise the production of products, such as fine chemicals, using a metabolically active cell, the culturing thereof in an aqueous medium and the workup of the product using a hydrophobic organic solution. In a preferred embodiment, the term "metabolically active cell", as used herein, may be understood as meaning a living cell with metabolic activity, preferably a cell that expresses or more preferably overexpresses an enzyme relevant for the biotechnological production of the product of interest in active form. The cell may be a prokaryote, including Archaea, or a eukaryote, and in the case of a prokaryote the cell is preferably selected from the group of genera comprising *Pseudomonas, Corynebacterium* and *Escherichia*. In an even more preferred embodiment, the cell may be a bacterial cell, even more preferably a Gram-negative bacterial cell, most preferably *E. coli*. In a further preferred embodiment the cell is a eukaryotic cell, more preferably a fungal cell, even more preferably a yeast cell, most preferably selected from *Saccharomyces* or *Candida, Pichia*, in particular *Candida tropicalis*. In a preferred embodiment the term "lower eukaryote", as used herein, describes a eukaryote that is unicellular in all phases of its existence, in contrast to higher eukaryotes, which spend the major part of their life in the form of a multicellular organism with tissues comprising differentiated cells. The term "cell" may be used, in a particular embodiment, synonymously and exchangeably with the term "microorganism" in this application. Furthermore, the cell may be an isolated cell or a mixture of different cells.

Numerous aqueous culture media are conventionally known to the person skilled in the art, which may be suitable for the maintenance or culturing of cells, in particular biotechnologically important cells. Among these are equally complete media such as LB media, minimal media such as M9 media as well as selective media, for example those that contain a high salt concentration and therefore, only make possible the growth of halophilic or at least halotolerant organisms. In a preferred embodiment the term "aqueous culture medium", as used herein, may be understood as meaning a reaction medium based on water, which with respect to all relevant factors, in particular pH, salt content and temperature, is constituted such that it maintains or promotes the viability of cells contained therein, preferably microorganisms, and both aqueous culture medium and hydrophobic organic phase are present in liquid form. The temperature demands of various biotechnologically important cells may be inferred from microbiological and molecular biological textbooks, e.g. Fuchs/Schlegl, 2008. In a preferred embodiment, the pH of the aqueous culture medium at the time of contacting may be between 4 and 9, more preferably between 4.5 and 8.5, most preferably between 6.5 and 7.5. In a further preferred embodiment, the temperature is between 0 and 45° C., more preferably between 15 and 40° C., most preferably between 20 and 37° C.

Solvents that may be used to prepare a hydrophobic organic solution are known to the person skilled in the art. In a preferred embodiment, the term "hydrophobic", as used herein, may be understood as meaning the property of a liquid of forming in the liquid state, in the presence of a liquid aqueous phase, a separate liquid phase clearly delineated from the aqueous phase. The latter can be a coherent liquid phase or an emulsion. In a further preferred embodiment, the term "hydrophobic", as used herein, may be understood as meaning the property of a compound of essentially not dissolving in water. Finally, "hydrophobic" may be understood as meaning in a further preferred embodiment, as used herein, that a designated compound of this type has a P value (J. Sangster, Octanol-Water Partition Coefficients Fundamentals and Physical Chemistry, Vol. 2 of Wiley Series in Solution Chemistry, John Wiley & Sons, Chichester, 1997), the decadic logarithm of which is greater than 0, preferably greater than 0.5, even more preferably greater than 1 and most preferably greater than 2. Preferred organic solvents comprise, but are not restricted to, solvents from the group including substituted and unsubstituted alkanes, cycloalkanes, cycloalkenes, aryls, fatty acids, fatty acid esters, alcohols, heterocycloalkanes, heterocycloalkenes and heteroaryls liquid at room temperature. The hydrophobic organic solution may also be a mixture comprising more than one hydrophobic organic solvent.

The β-oxidation of fatty acids is a widespread metabolic pathway that equally allows prokaryotic and eukaryotic organisms to oxidize fatty acids and to make the chemical energy contained therein available to the metabolism (Fujita et al., 2007). In a broader sense, it begins with the uptake of a fatty acid into the cell, in the case of *E. coli* by the transporter FadL (Black, 1991), which channels it through the outer and inner membrane of the Gram-negative bacterial cell and the FadD gene product (Black et al., 1992), which releases the fatty acid in the form of the CoA ester into the cytosol. There the fatty acid, if the conditions necessitate it, is firstly oxidized at the β-position of the CoA-fatty acid ester by an acyl-CoA dehydrogenase, in the case of *E. coli* FadE (Campbell and Cronan, 2002). A similar molecule can alternatively also be formed from a doubly unsaturated fatty acid by reduction by means of a 2,4-dienoyl-CoA reductase, with *E. coli* FadH. A multifunctional enzyme, enoyl-CoA hydratase/3-hydroxyacyl-CoA dehydrogenase, with *E. coli* FadB subsequently catalyses the hydration with formation of the secondary alcohol and its subsequent oxidation to the ketone. In the last step a 3-ketoacyl-CoA thiolase, in the case of *E. coli* FadA, catalyses the cleavage of the ketoacyl-CoA with the result that acetyl-CoA and a CoA ester of the fatty acid shorter by two carbon atoms in comparison to the starting molecule are released. If it is not likewise acetyl-CoA, the latter can again be fed into the β-oxidation cycle and shortened with oxidation. FadR, a regulator of the Fad operon, is also involved in the regulation of the β-oxidation of fatty acids, which comprises the genes necessary for the degradation of fatty acids, without FadR catalysing a reaction of the β-oxidation. In a preferred embodiment, the term "enzyme that catalyses one of the reactions of the β-oxidation of fatty acids" may be understood as meaning any enzyme that interacts directly with the fatty acid substrate or a molecule resulting therefrom on the pathway to the acetyl-CoA, preferably recognizes it as a substrate, and catalyses its conversion to a metabolic product lying closer to the acetyl-CoA on this degradation pathway, preferably including the fatty acid importer, which brings about the uptake of the fatty acid into the cell. For example, the acyl-CoA dehydrogenase counts among these enzymes according to the preceding definition since it interacts with the fatty acid CoA ester and catalyses its conversion to the enoyl-CoA, which lies closer to the acetyl-CoA than the fatty acid CoA ester on the metabolic pathway of the β-oxidation. In a particularly preferred embodiment, the term "enzyme that catalyses one of the reactions of the β-oxidation of fatty acids", as used herein, is understood as meaning any enzyme from the group that comprises the gene products FadA, FadB, FadD, FadL and FadE from *E. coli* and/or their variants or homologues from other organisms. The gene products FadA, FadB, FadD, FadL and FadE from *E. coli* as well as variants and homologues from numerous other biotechnologically utilizable organisms and their nucleic acid and polypeptide sequences are described in the prior art, for example FadA under accession number AP009048.1, FadB under accession number BAE77457.1, FadD under accession number BAA15609.1, FadE under accession number BAA77891.2 and FadL under accession number BAA16205.1.

The present invention may not only be carried out or applied using the or on the exact amino acid or nucleic acid sequences of the biological macromolecules described herein, for example by knockout of a gene that codes for an enzyme catalysing one of the reactions of the β-oxidation, but also with use of or on variants of such macromolecules that may be obtained by deletion, addition or substitution of one or more amino acids or nucleic acids. In a preferred embodiment, the term "variant" denotes a nucleic acid sequence or amino acid sequence, used below synonymously and exchangeably with the term "homologue", as used herein, another nucleic acid or amino acid sequence, which with respect to the corresponding original wild-type nucleic acid or amino acid sequence has a homology, used synonymously here with identity, of 70, 75, 80, 85, 90, 92, 94, 96, 98, 99% or more percent, preferably other than the amino acids forming the catalytically active centre or amino acids essential for the structure or folding being deleted or substituted or the latter only being substituted conservatively, for example a glutamate instead of an aspartate or a leucine instead of a valine. Algorithms that may be used to calculate the extent of homology of two sequences, e.g. Arthur Lesk (2008), Introduction to bioinformatics, 3rd edition, are known. In a further more preferred embodiment of the present invention, the variant of an amino acid or nucleic acid sequence, preferably additionally to the abovementioned sequence homology, may have essentially the same enzymatic activity of the wild-type molecule or of the original molecule. For example, a variant of a polypeptide enzymatically active as a protease has the same or essentially the same proteolytic activity as the polypeptide enzyme, i.e. the ability to catalyse the hydrolysis of a peptide bond. In a particular embodiment, the term "essentially the same enzymatic activity" means an activity with respect to the substrates of the wild-type polypeptide that is clearly above the background activity or/and differs by less than 3, more preferably 2, even more preferably an order of magnitude from the KM and/or kcat values that the wild-type polypeptide has with respect to the same substrates. In a further preferred embodiment, the term "variant" comprises a nucleic acid or amino acid sequence at least of one active part or fragment of the nucleic acid or amino acid sequence. In a further preferred embodiment, the term "active part", as used herein, denotes an amino acid sequence or a nucleic acid sequence that has a smaller length than the full length of the amino acid sequence or codes for a smaller length than the full length of the amino acid sequence, the amino acid sequence or the encoded amino acid sequence with a smaller length than the wild-type amino acid sequence essentially having the same enzymatic activity as the wild-type polypeptide or a variant thereof, for example as a fatty acid importer, as an enoyl-CoA hydratase or FadE or as an acetyl-CoA acyltransferase or FadB. In a particular embodiment, the term "variant" of a nucleic acid comprises a nucleic acid, the complementary strand of which binds to the wild-type nucleic acid, preferably under stringent conditions. The stringency of the hybridization reaction is easily determinable for the person skilled in the art and in general depends on the length of the probe, the temperatures during washing and the salt concentration. In general, longer probes need higher temperatures for hybridizing, whereas shorter probes manage with low temperatures. Whether hybridization takes place in general depends on the ability of the denatured DNA to fuse to complementary strands that are present in their environment, namely below the melt temperature. The stringency of the hybridization reaction and corresponding conditions are described in more detail in Ausubel et al. 1995. The person skilled in the art may find instructions for the identification of DNA sequences by means of hybridization, inter alia, in the handbook "The DIG System Users Guide for Filter Hybridization" of Boehringer Mannheim GmbH (Mannheim, Germany, 1993) and in Liebl et al. (International Journal of Systematic Bacteriology 41: 255-260 (1991)). Hybridization takes place under stringent conditions in a preferred embodiment, that is only hybrids are formed in which the probe and target sequence, i.e. the polynucleotides treated with the probe, are at least 70% identical. It is known that the stringency of the hybridization including the washing steps is influenced or determined by varying the buffer composition, the temperature and the salt concentration. The hybridization reaction may in general be carried out with relatively low stringency in comparison to the washing steps (Hybaid Hybridisation Guide, Hybaid Limited, Teddington, UK, 1996). For the hybridization reaction, for example, a buffer corresponding to 5×SSC buffer at a temperature of about 50° C.-68° C. may be employed. Probes may also hybridize with polynucleotides that have less than 70% identity to the sequence of the probe. Such hybrids are less stable and are removed by washing under stringent conditions. This may be achieved, for example, by reducing the salt concentration to 2×SSC and optionally subsequently 0.5×SSC (The DIG System User's Guide for Filter Hybridisation, Boehringer Mannheim, Mannheim, Germany, 1995), a temperature of, in the sequence of increasing preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. being set. Temperature ranges of about 64° C.-68° C. or about 66° C.-68° C. are preferred. It is optionally possible to reduce the salt concentration to a concentration corresponding to 0.2×SSC or 0.1× SSC. By stepwise increase in the hybridization temperature in steps of about 1-2° C. from 50° C. to 68° C. polynucleotide fragments can be isolated, which, for example, in the sequence of increasing preference, have at least 70% or at least 80% or at least 90%, at least 91%, at least 92%, at least 93%, at least 94%, at least 95%, at least 96%, at least 97%, at least 98% or at least 99% identity to the sequence of the nucleic acid molecule employed. Further instructions for hybridization are obtainable on the market in the form of "kits" (e.g. DIG Easy Hyb from Roche Diagnostics GmbH, Mannheim, Germany, Catalogue No. 1603558). In a preferred embodiment, the term "variant" of a nucleic acid, as used herein, comprises any desired nucleic acid sequence that codes for the same amino acid sequence as the original nucleic acid or a variant of this amino acid sequence in the context of the degeneracy of the genetic code.

With the development of modern genetic, microbiological and molecular biological methods, numerous tools are available to the person skilled in the art, with which he can routinely measure and influence the activity of enzymes present in living cells. For the determination of the activity of an enzyme that is present in the form of a suspension, of a pellet or can be removed from a cell culture in processed form, enzymatic standard tests can be used and evaluated, as is described in textbooks, for example Cornish-Bowden, 1995. The prior art discloses numerous tests that are especially suitable for the measurement of the activity of enzymes that catalyse one of the reactions of the β-oxidation of fatty acids, for example in Kameda & Nunn (1981), Marrakchi et al. (2003), Lobo et al. (2001) and Xu et al. (2011). Routinely applicable methods for decreasing the activity of an enzyme in a cell, for example by undirected mutagenesis of cells by exposure to radioactive radiation followed by enrichment or screening of the mutants, by site-directed introduction of point mutations or by the knockout of a gene coding for an active enzyme chromosomally integrated into a cell are also described in the prior art, for example in Maniatis et al. (1989) or in Fuchs & Schlegl (2007). In the particular case of the Fad gene product, the overexpression of a transcriptional repressor, for example of FadR, also lends itself to lowering the activity (Fujita et al., 2007). A reduction of activity based on RNA interference (Tuschl, 2001) or using specific inhibitors is also possible. In a preferred embodiment, the formulation "the cell having a decreased activity, compared to its wild-type", of an enzyme, as according to the present invention, means that the activity of the enzyme is reduced in the modified cell compared to the activity of the same enzyme in a wild-type cell. In a preferred embodiment, the relative reduction in the sequence of increasing preference is 5, 10, 20, 40, 50, 75, 90, 95, 99 or more percent of the activity. In a particularly preferred embodiment, activity of the enzyme cannot be distinguished from that of the background.

In the second step of the process according to the invention, contacting of the aqueous culture medium with a hydrophobic organic solution occurs. In a preferred embodiment of the present invention, the term "contacting", as used herein, means that aqueous culture medium and organic solution are brought directly into contact without a mechanical barrier insurmountable for an aqueous culture medium and/or a hydrophobic organic solution, for example an inorganic membrane, being interposed. For example, the aqueous culture medium may be introduced into a fermenter, and the organic solution may be added to the culture medium in the same fermenter, such that both liquids mix. In a preferred embodiment, the contacting may take place at least partially with stirring, the inflow of gas or similar measures that are suitable for increasing the contact area of the two phases.

After the contacting step, the hydrophobic organic solution is separated off from the aqueous culture medium. On account of the inherent ability of this system to form two phases, this is a process that can easily be carried out for the person skilled in the art, which can proceed simply by allowing the vessel to stand and subsequently decanting off one phase. Alternatively, a separating funnel can be used. In the case of sufficiently different boiling points, the possibility exists of stripping off the phase boiling at lower temperatures, which is generally the organic phase, by applying reduced pressure. Small amounts of water remaining in the organic phase can be removed by using inorganic drying agents such as calcium hydride, anhydrous calcium chloride, silica gel, anhydrous sodium sulphate, sodium hydroxide or the like.

The process according to the invention may be conducted using customary hydrophobic organic solvents that includes substituted and unsubstituted alkanes, cycloalkanes, cycloalkenes, aryls, fatty acids, fatty acid esters, alcohols, heterocycloalkanes, heterocycloalkenes and heteroaryls liquid at room temperature. Hydrophobic organic solvents that are not Liquid per se may also be suitable, provided they are part of a mixture of solvents that is liquid in its entirety. Considering that numerous solvents may have a more or less toxic action on metabolically active cells, appropriate moderate concentrations or even concentrations of the hydrophobic organic solvent having a non-toxic effect may be preferred, so that the cells thus at least temporarily retain their metabolic activity. In a particularly preferred embodiment, the solvent may be a saturated or unsaturated fatty acid having at least eight, preferably at least twelve carbon atoms, for example lauric acid, oleic acid or erucic acid or the methyl esters thereof. In a further preferred embodiment, the solvent may be a fatty acid of the formula $CH_3-(CH_2)_x-COOH$, where x can be 8, 9, 10, 11, 12, 13, 14, 15, 16, 17, 18, 19, 20, 21, 22 or more. In a further preferred embodiment, the solvent may be an unsaturated fatty acid having a double bond, particularly preferably one in position 9, particularly preferably oleic acid. In a further particularly preferred embodiment, the solvent may be hexanoic acid.

The volume of the hydrophobic organic solution may be selected such that the organic phase may easily be separated off and in a preferred embodiment, the volume of the organic solution may be 2 to 98, more preferably 5 to 95, even more preferably 10 to 40, most preferably 20 to 30 percent of the total volume of aqueous culture medium and hydrophobic organic solution.

As a metabolically active cell, generally a cell is selected that may be able to produce a product of particular interest. The use of a recombinant cell may be particularly advantageous. In a preferred embodiment, the term "recombinant" may be understood as according to the present invention as meaning that the nucleic acid molecule, designated as recombinant, introduced into the "recombinant cell" is a nucleic acid molecule not taken from nature, but a nucleic acid molecule produced using a molecular, biological or chemical synthesis process or that the cell designated as recombinant comprises a recombinant nucleic acid molecule or a polypeptide encoded therefrom. Molecular biological routine processes for preparing recombinant nucleic acid molecules and cells are known, for example in Sambrook et al. (1989) or Schlegl & Fuchs (2007).

It may be furthermore particularly advantageous if the cell contains or, particularly preferably, over-expresses an enzyme producing a product or a precursor or intermediate thereof. This may be achieved by introducing a vector that comprises a nucleic acid molecule coding for the enzyme by transformation or the like into the cell or incorporating the nucleic acid molecule coding for the enzyme into the genetic make-up of the cell, for example a chromosome. For numerous biotechnologically important types of cells, e.g. *E. coli*, suitable processes and vectors are known that can be used for the expression or overexpression of a nucleic acid molecule, for example the vectors of the type pET or pGEX and cells suitable for their expression (Moffatt & Studier (1986), Rosenberg et al. (1987) and Studier et al. (1990).

The process according to the invention may be particularly useful when a metabolically active cell is used to metabolize a hydrophobic organic solvent or to catalyse a chemical reaction using the hydrophobic organic solvent as a substrate. These enzymes include the alkane hydroxylases.

In a particularly preferred embodiment, an "alkane hydroxylase", as according to the present invention, is an enzyme that catalyses the oxidation of an alkane to the alcohol aldehyde/ketone and/or to the carboxylic acid, preferably mainly to the alcohol. Alkane hydroxylases are described extensively, for example in Grant et al. (2011) or Koch et al. (2009). In a particularly preferred embodiment, the alkane hydroxylase is an "alkane hydroxylase of the alkB type". AlkB is an oxidoreductase from the AlkBGT system of *Pseudomonas putida*, which is known for its hydroxylase activity. This is dependent on two further polypeptides, AlkG and AlkT. AlkT is characterized as a FAD-dependent rubredoxin reductase that transfers electrons from NADH to AlkG. AlkG is a rubredoxin, an iron-containing redox protein, which functions as a direct electron donor for AlkB. In a preferred embodiment, the term "alkane hydroxylase of the alkB type", as according to the present invention, may be understood as meaning a membrane-bound alkane hydroxylase. In a further preferred embodiment, the same term "alkane hydroxylase of the alkB type" may be understood as meaning a polypeptide having a sequence homology of increasingly preferably at least 75, 80, 85, 90, 92, 94, 96, 98 or 99% to the sequence of the AlkB of *Pseudomonas putida* Gpol (database code: CAB54050.1, this and all other database codes used in this document originate from the gene bank protein database of the NCBI in the release available on 9 Nov. 2011). The term "sequence", as used herein, can relate to the amino acid sequence of a polypeptide and/or the nucleic acid sequence coding for this.

The process may be used firstly to oxidize and subsequently to aminate fatty acids or their esters. An enzyme system as is described in the international patent application WO 2009/077461, for example, may be suitable for this. The metabolically active cell may be a cell that contains a recombinant alkane hydroxylase and a transaminase, preferably moreover at least one enzyme from the group comprising alcohol dehydrogenase, alanine dehydrogenase and lactam hydrolase. In a preferred embodiment, the term "alcohol dehydrogenase", as according to the present invention, may be understood as meaning an enzyme that oxidizes an aldehyde or ketone to the corresponding primary or secondary alcohol. Examples comprise the alcohol dehydrogenases of *Ralstonia eutropha* (ACB78191.1), *Lactobacillus brevis* (YP_795183.1), *Lactobacillus kefiri* (ACF95832.1), of horse liver, of *Paracoccus pantotrophus* (ACB78182.1) and *Sphingobium yanoikuyae* (EU427523.1) as well as the respective variants thereof. In a preferred embodiment, the term "transaminase", as according to the present invention, may be understood as meaning an enzyme that catalyses the transfer of α-amino groups from a donor molecule, preferably an amino acid, to an acceptor molecule, preferably an β-ketocarboxylic acid. For example, the transaminase of *Chromobacterium violaceum* ATCC 12472 (database code NP_901695) can be used. In a preferred embodiment, the term "alanine dehydrogenase", as used herein, is understood as meaning an enzyme that catalyses the conversion of L-alanine with consumption of water and NAD+ to pyruvate, ammonia and NADH. For example, the alanine dehydrogenases from *Bacillus subtilis* (database code L20916), *Rhizobium leguminosarum* (database code CP001622), *Vibrio proteolytikus* (database code AF070716), *Mycobacterium tuberculosis* (database code X63069), *Enterobacter aerogenes* (database code AB013821) may be used.

The present invention provides not only the enzymatic two-phase system process as described above and in the Claims, but provides the use of a knockout of an enzyme that catalyses one of the reactions of the β-oxidation of fatty acids, preferably of an enzyme selected from the group comprising FadA, FadB, FadD, FadE and FadL, more preferably FadE, as part of the genetic make-up of a metabolically active cell for improving the separation of a hydrophobic organic solution from an aqueous culture medium comprising the metabolically active cell. If the necessity thus exists in the context of any desired process to separate a hydrophobic organic solution from an aqueous culture medium comprising a metabolically active cell, instead of a metabolically active cell without appropriate modification of the fatty acid metabolism, that is a cell with unchanged or even increased activity, compared to its wild-type, of the enzymes that catalyse a reaction of the β-oxidation of fatty acids, preferably of the group including FadA, FadB, FadD, FadE and FadL, more preferably FadE, according to the invention a cell is to be used in which at least one enzyme that catalyses one of the reactions of the β-oxidation of fatty acids is knocked out, preferably an enzyme selected from the group comprising FadA, FadB, FadD, FadE and FadL, more preferably FadE.

This knockout of a Fad gene may be used independently of whether the metabolically active cell is to be used for the production of a fatty acid or a derivative thereof or of another molecule that may be degraded by the metabolic pathway of the β-oxidation.

In a preferred embodiment, the term "knockout", as according to the present invention, may be understood as meaning that the transcription and/or translation of the gene or its gene product in comparison to the wild-type cell is reduced, for example by deletion of a part of or of the whole gene, by insertion of a stop codon in a suitable site, by removal of an essential part of the promoter or by removal of the ribosomal binding site.

In a most preferred embodiment, the process according to the invention comprises the a) provison of an aqueous culture medium comprising a metabolically active cell, contacting of the aqueous culture medium with a hydrophobic organic solution and separation of the hydrophobic organic solution from the aqueous culture medium. The metabolically active cell has a decreased activity, compared to its wild-type, of FadE or a variant thereof, in which the metabolically active cell is a recombinant strain of *E. coli* that contains a recombinant alkane hydroxylase, preferably AlkBGT from *Pseudomonas putida* or a variant thereof, as well as a recombinant transaminase, and the hydrophobic organic solvent comprises a mixture of lauric acid or hexanoic acid or the methyl ester thereof and an unsaturated fatty acid, preferably oleic acid or erucic acid, most preferably oleic acid. The ratio of oleic acid or erucic acid to lauric acid or hexanoic acid or the methyl ester thereof may be from 20:80 to 80 to 20, preferably 20:80 to 40:60.

In a most preferred embodiment, the process according to the invention may be a process for production of an β-aminocarboxylic acid comprising preparing an aqueous culture medium of a metabolically active cell having a decreased activity; contacting of the aqueous culture medium with a hydrophobic organic solution comprising a substrate for biotransformation; conducting a biotransformation of the substrate; and separating the hydrophobic organic solution comprising a biotransformed substrate from the aqueous culture medium; wherein the decreased activity of the metabolically active cell is in comparison to a wild-type of the active cell, and the decreased activity is of at least of one enzyme that catalyses one reaction of β-oxidation of fatty acids, the cell preferably being *E. coli* and the enzyme that catalyses one of the reactions of the β-oxidation of fatty acids being FadE, and the cell moreover being genetically modified such that it produces an increased amount of β-aminocarboxylic acid compared to its wild-type, preferably in that it is equipped with a system of recombinant enzymes comprising an alkane hydroxylase, preferably AlkBGT from *Pseudomonas putida*, optionally an alcohol dehydrogenase and a β-transaminase. In a further most preferred embodiment, the invention provide a cell that has a decreased activity, compared to its wild-type, at least of one enzyme which catalyses one of the reactions of the β-oxidation of fatty acids, the cell may preferably be *E. coli* and the enzyme that catalyses one of the reactions of the β-oxidation of fatty acids may be FadE, and the cell moreover being genetically modified such that, compared to its wild-type, it produces an increased amount of β-aminocarboxylic acid, preferably in that it is equipped with a system of recombinant enzymes comprising an alkane hydroxylase, preferably AlkBGT from *Pseudomonas putida*, optionally an alcohol dehydrogenase and a β-transaminase.

The present invention is furthermore illustrated by the following figures and non-restricting examples, from which further features, embodiments, aspects and advantages of the present invention may be inferred.

FIG. 1 shows differences in the phase separation in the production of ALAME using the ΔFadE mutant W3110 ΔFadE [alkB-alaD-TA] (also designated as "ΔFadE" below) (left) and the identical strain W3110 [alkB-alaD-TA], apart from the absence of the ☐FadE deletion (also designated as the wild-type ("WT") below) (right). The arrow shows the clear separation of the organic and of the aqueous phase with the mutant after ten minutes, whereas when using the other strain phase separation is still not discernible after the same time.

Figure 2:
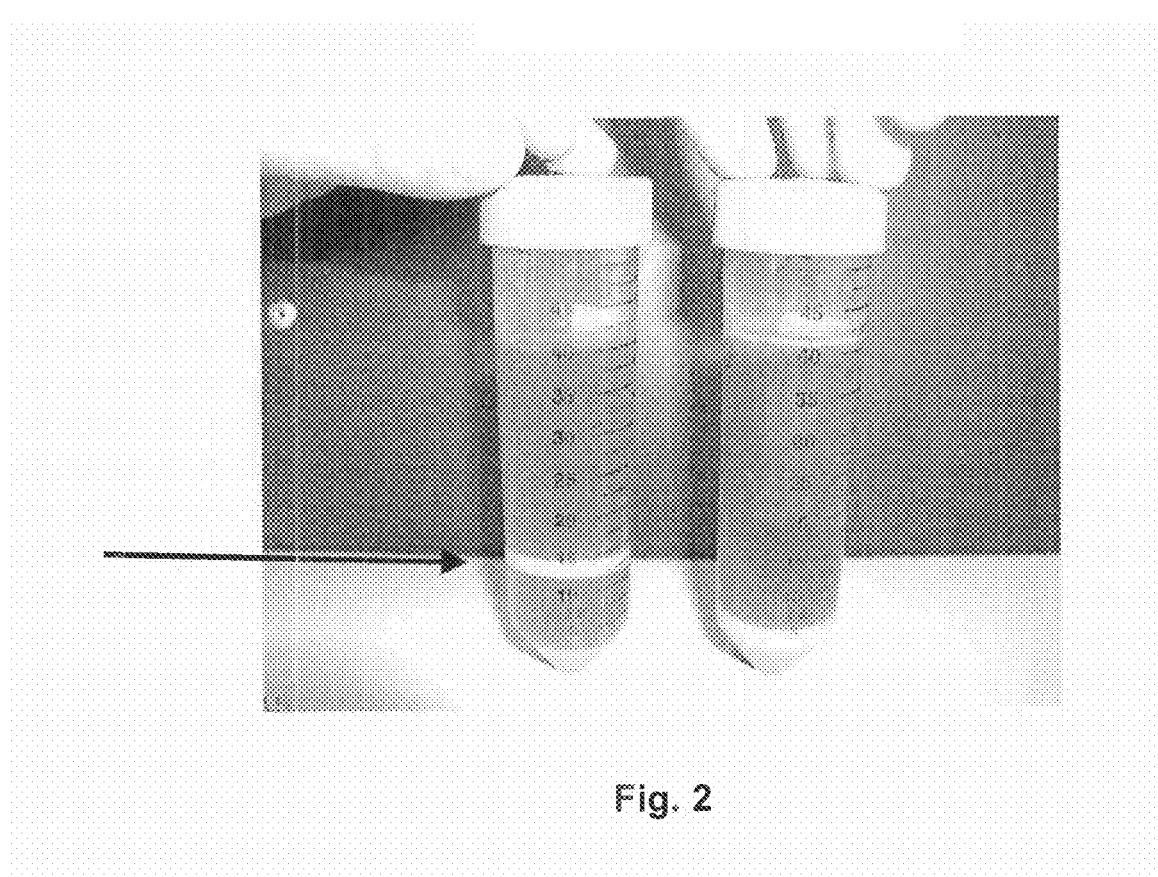
FIG. 2 shows the same experiment as FIG. 1 placed in a different container for observation.

FIG. 2 shows the same experiment as FIG. 1, apart from the fact that the reaction medium was filled into Falcon tubes after the fermentation.

Figure 3:
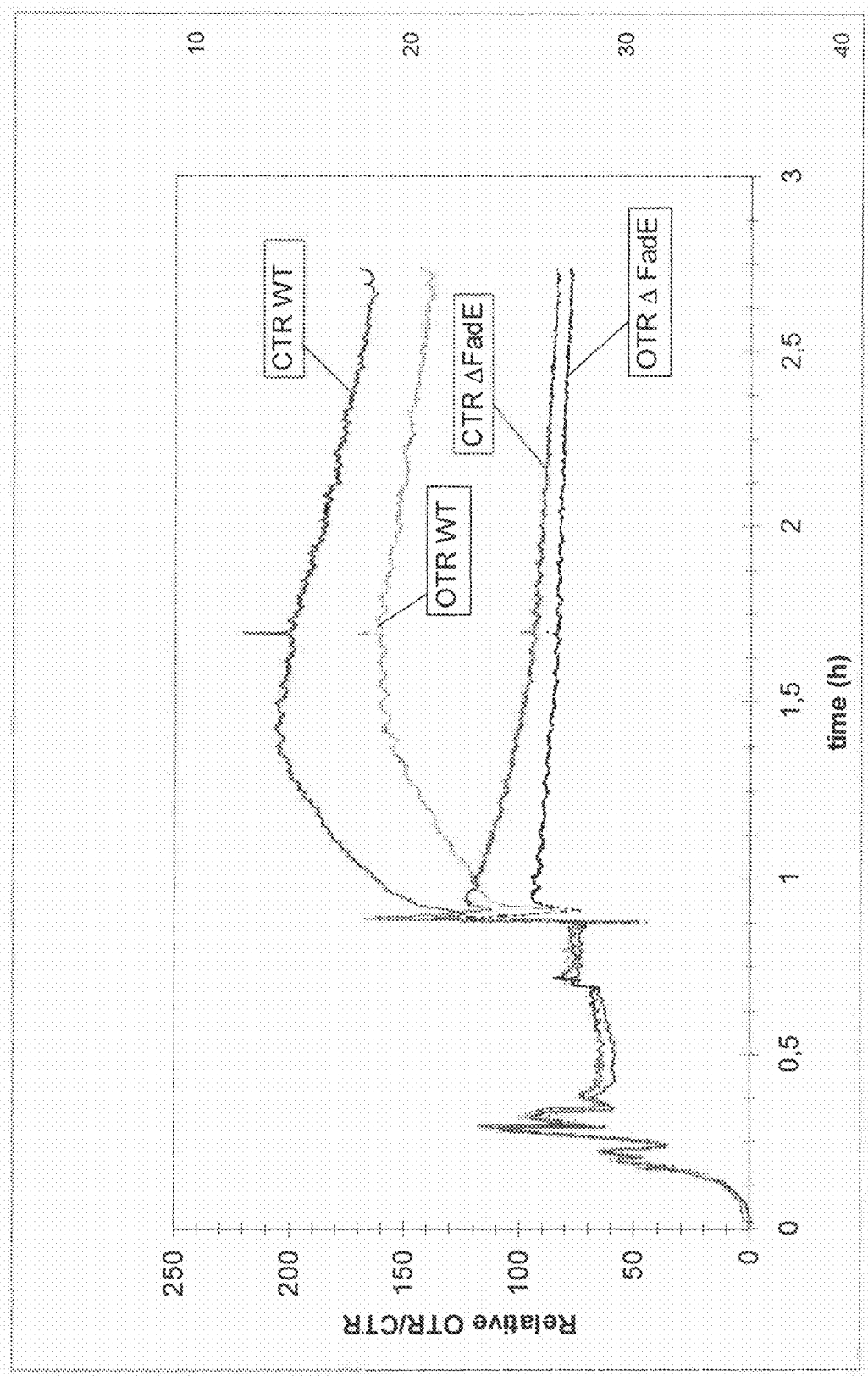
FIG. 3 shows a comparison of the oxygen transfer rates and carbon dioxide transfer rates for the experiments described in Example 1.

FIG. 3 shows the oxygen input in the form of the OTR (oxygen transfer rate) and the carbon dioxide output in the form of the CTR (carbon dioxide transfer rate) of both strains in the same experiment as in FIG. 1.

Figure 4:
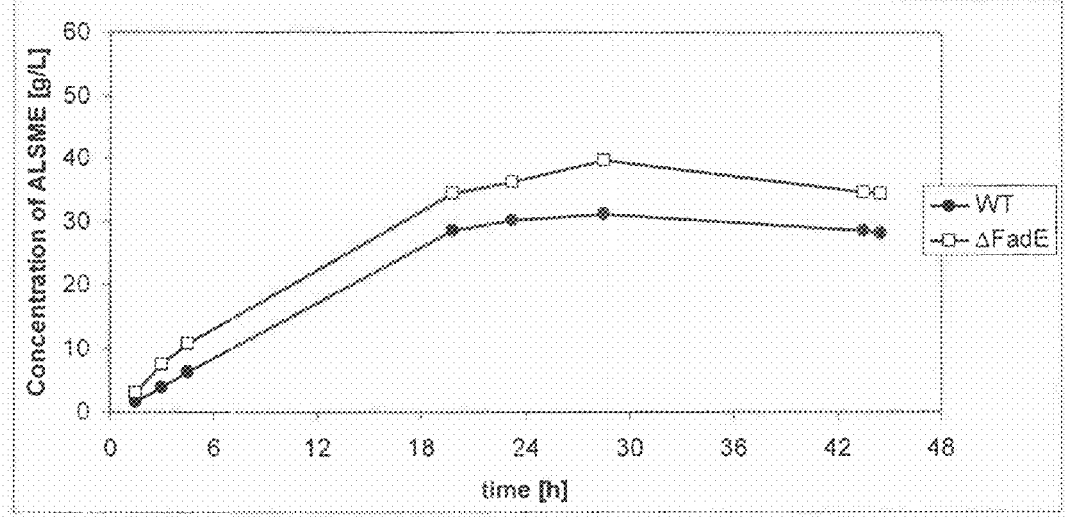
FIG. 4 shows the concentration of ALSME for the experiments described in Example 1.
Figure 5A:
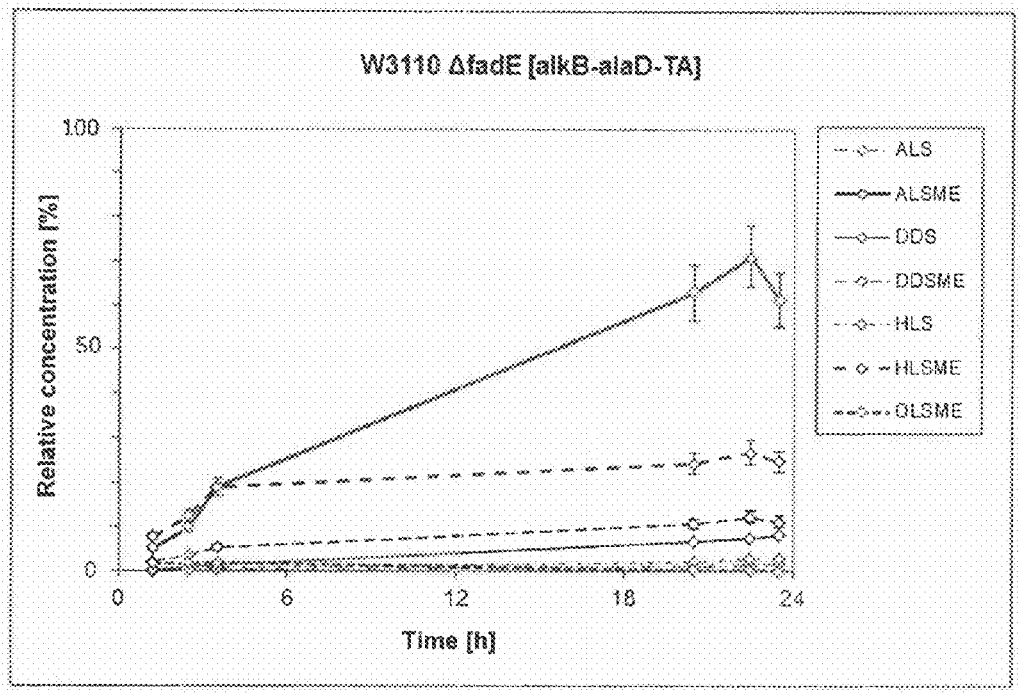
FIG. 5a shows the concentration of products obtained by the method according to the invention in Example 2.
Figure 5B:
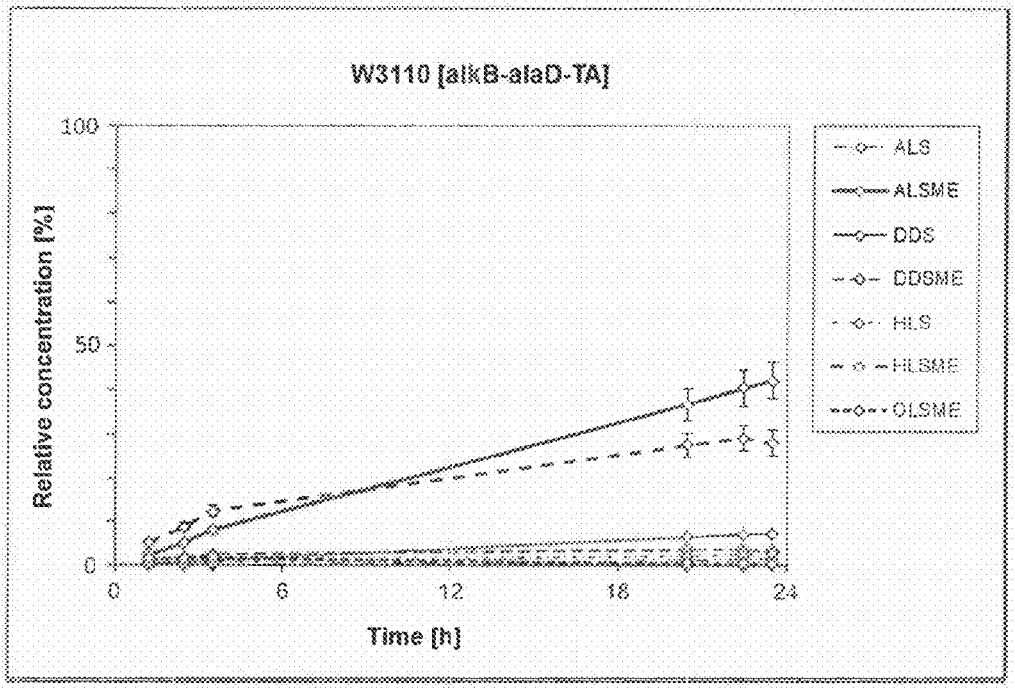
FIG. 5b shows the concentration of products obtained by the method not according to the invention in Example 2.
Figure 5C:
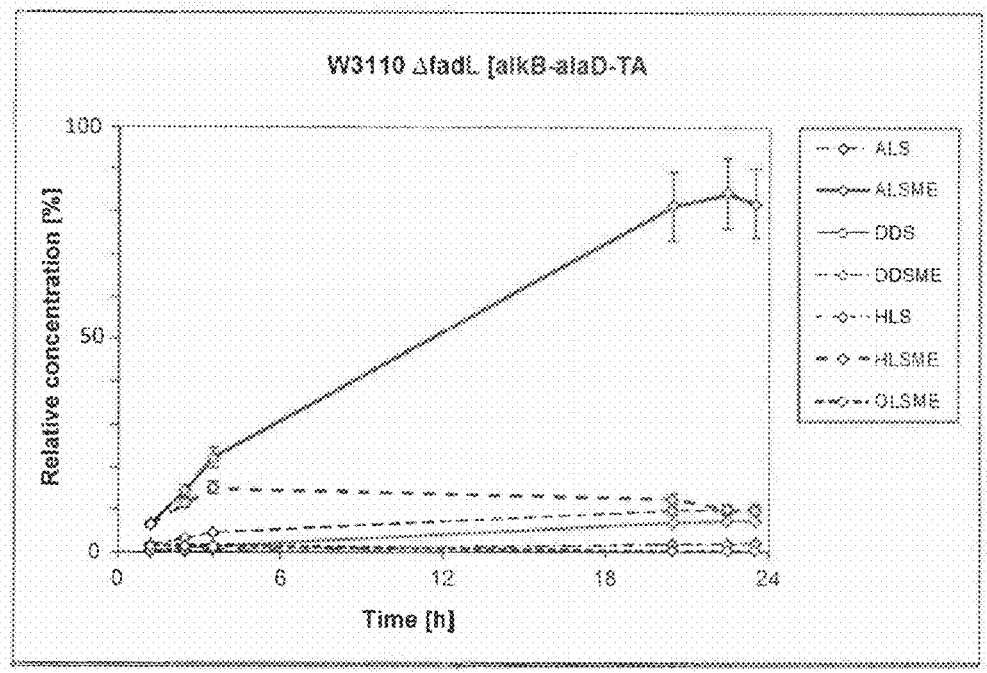
FIG. 5c shows the concentration of products obtained by the method according to the invention using a different strain in Example 2.
Figure 5D:
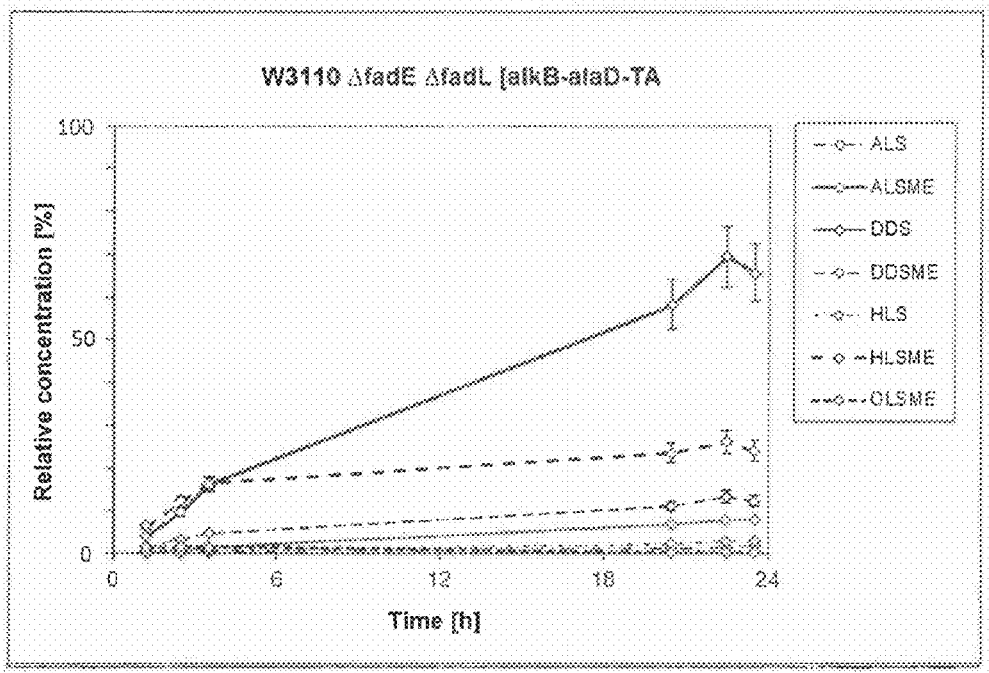
FIG. 5d shows the concentration of products obtained by the method according to the invention using another different strain in Example 2.

FIG. 4 shows the concentrations of ALAME over time in the medium in the same experiment as in FIG. 1.

FIG. 5 shows the concentration of various products in the reaction of lauric acid methyl ester (LAME) as described in Example 2, namely aminolauric acid (ALA), aminolauric acid methyl ester (ALAME), ω-carboxylauric acid (DDA), ω-carboxylauric acid methyl ester (DDAME), ω-hydroxylauric acid (HLA), ω-hydroxylauric acid methyl ester (HLAME) and ω-oxolauric acid (OLA). As strains, the Δ FadE strain (FIG. 5a), the wild-type (W3110) (FIG. 5b), the Δ FadL strain (FIG. 5c) and a strain containing Δ FadE and Δ FadL (FIG. 5d) were investigated.

Figure 6A:
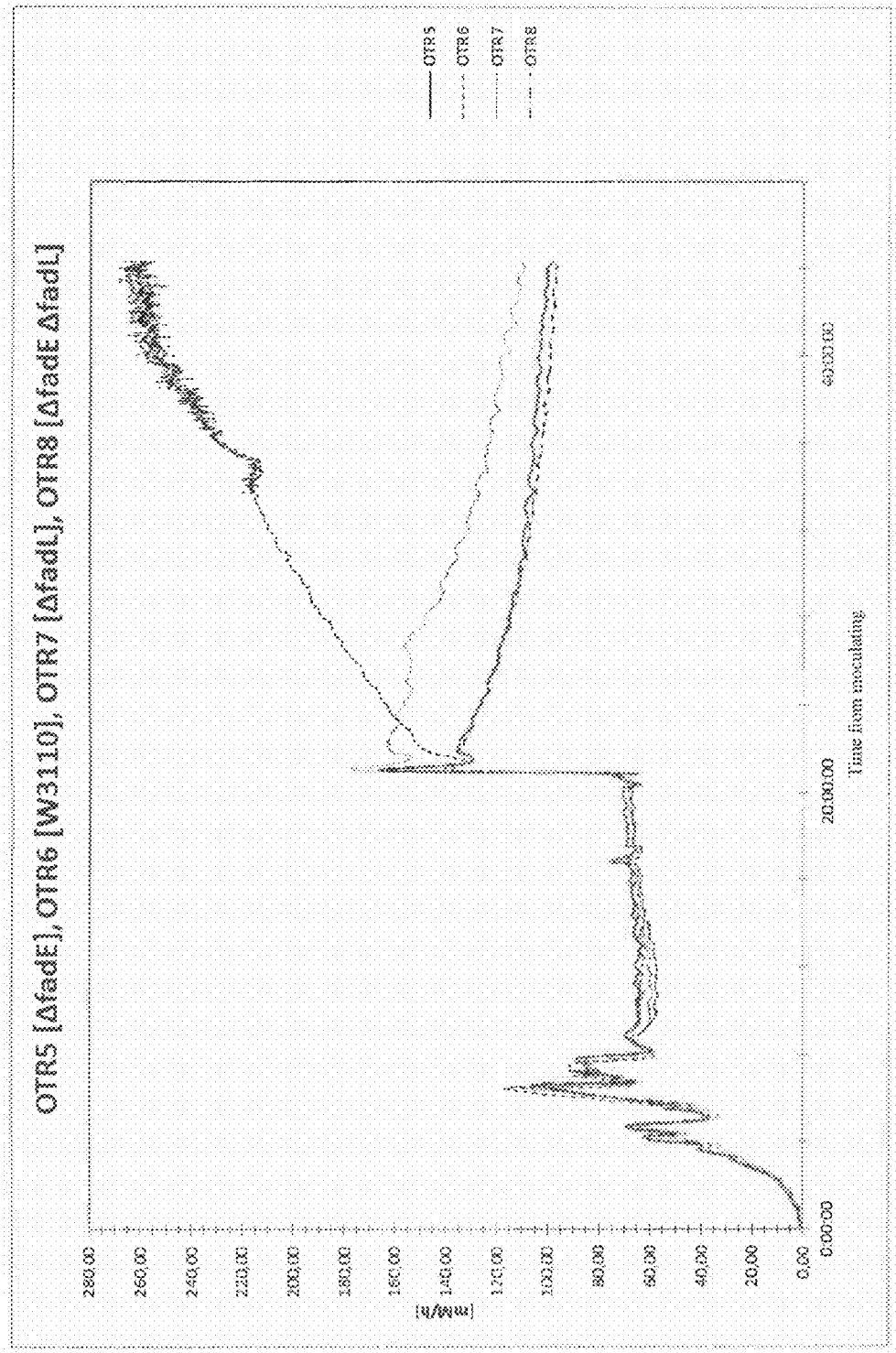
FIG. 6a shows the OTR curve for the experiment of Example 2.
Figure 6B:
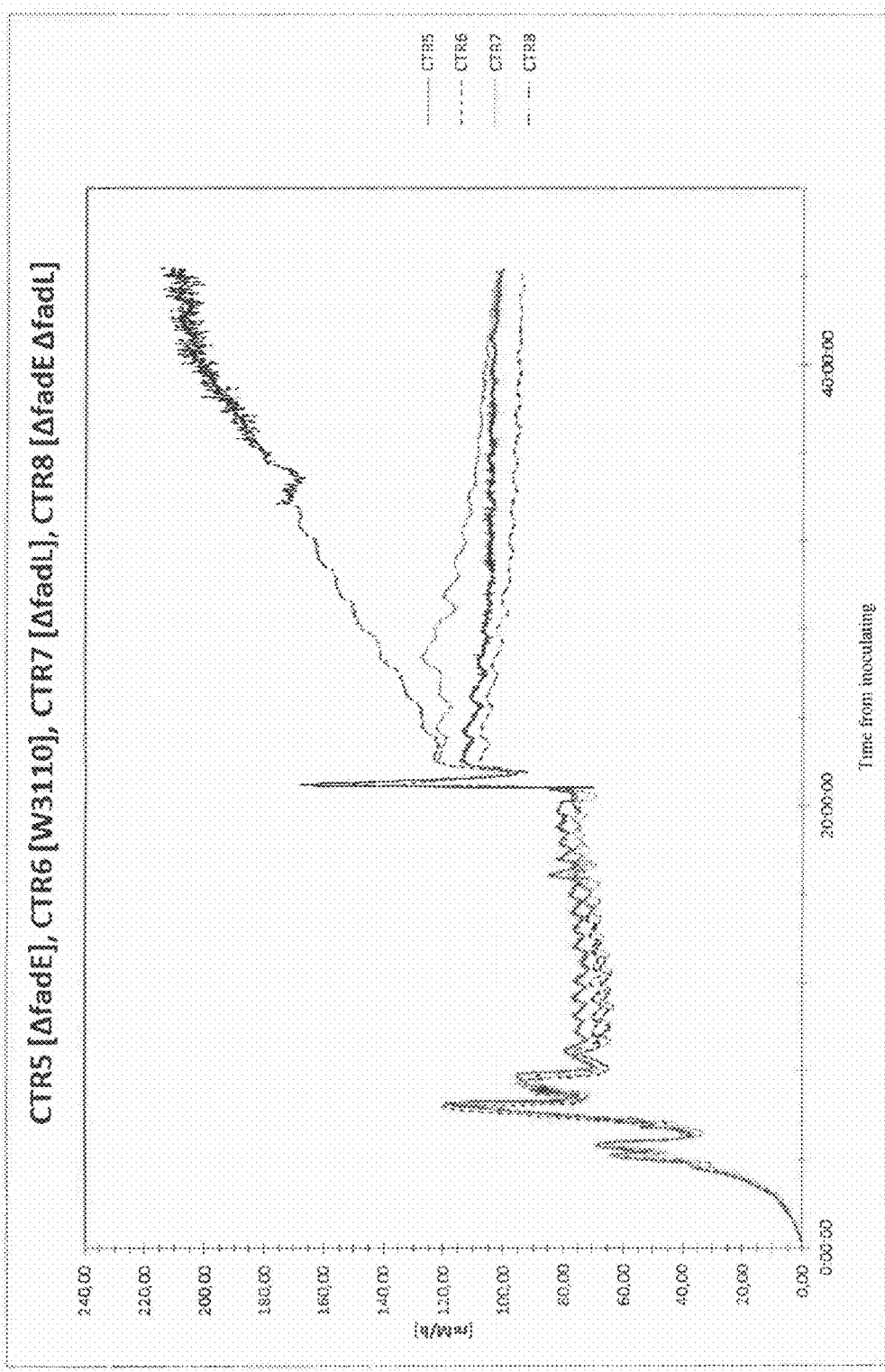
FIG. 6b shows the CTR curve for the experiment of Example 2.

FIG. 6 shows the OTR (FIG. 6a) and CTR (FIG. 6b) curves for the experiment described in Example 2.

Figure 7:
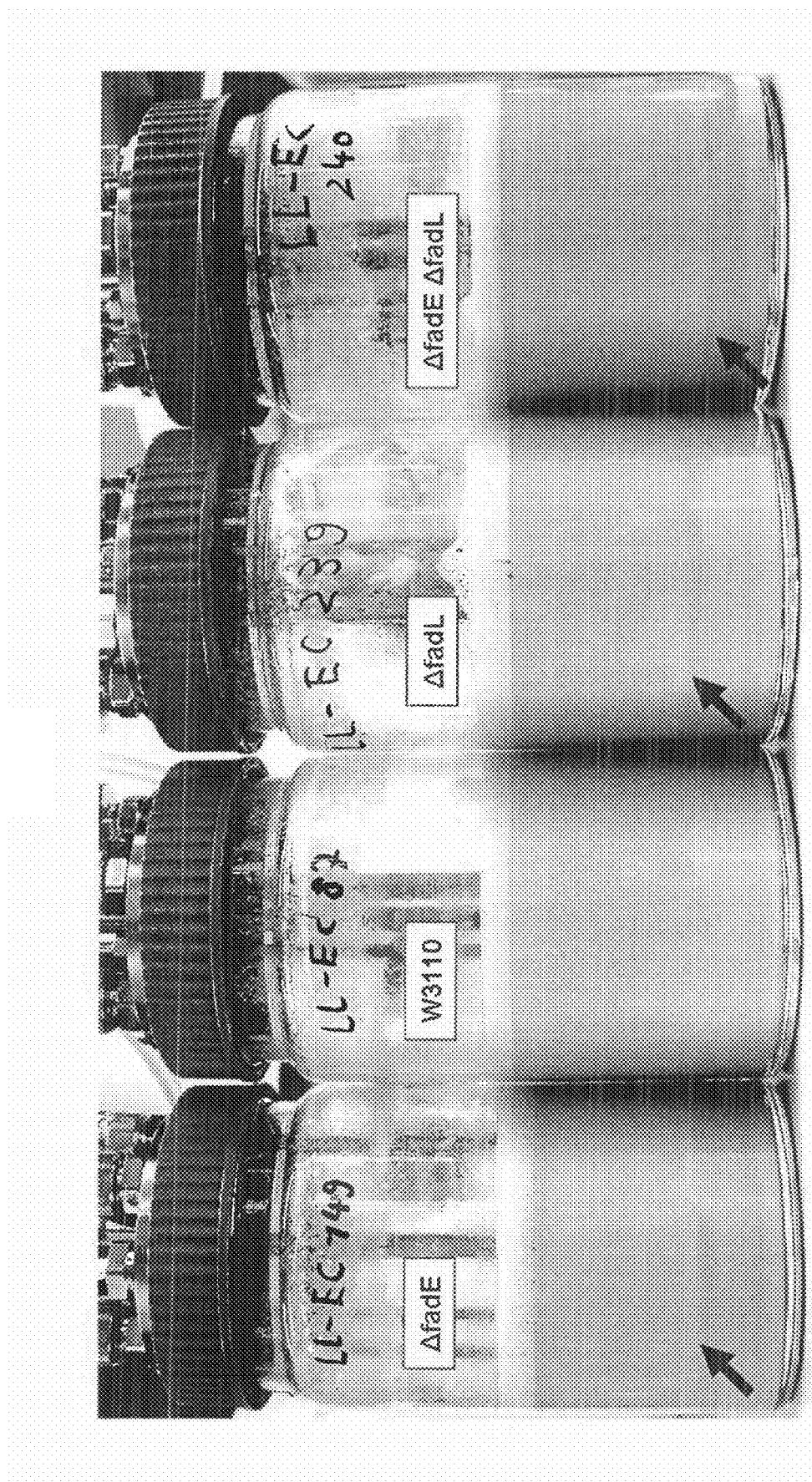
FIG. 7 shows the differences in phase separation obtained in Example 2.

FIG. 7 shows differences were observed in the phase separation in the production of ALAME using the Δ FadE, wild-type (W3110), Δ FadL and Δ FadE/Δ FadL strain in Example 2. The arrows show the clear separation of the organic and the aqueous phase with the mutants after ten minutes, whereas when using the wild-type strain phase separation is still not discernible after the same time.

Having generally described this invention, a further understanding can be obtained by reference to certain specific examples which are provided herein for purposes of illustration only, and are not intended to be limiting unless otherwise specified.

EXAMPLES

Example 1

Acceleration of the separation of an aqueous from a hydrophobic phase using a Δ FadE mutant in the biotechnological production of aminolauric acid methyl ester The biotransformation of lauric acid methyl ester to aminolauric acid methyl ester was carried out in the 8-fold parallel fermentation system of DASGIP using the strains W3110Δ FadE [alkB-alaD-TA] and W3110 [alkB-alaD-TA]. W3110 [alkB-alaD-TA] is a strain of *E. coli* W3110 that comprises a pBR322-based plasmid with an oxidation and transamination system comprising oxidoreductase AlkB, alanine dehydrogenase and transaminase, as is described in WO2009077461. W3110 Δ FadE [alkB-alaD-TA] is identical with the latter strain, apart from the fact that the gene coding for FadE is deleted and the strain thus has no acyl-CoA dehydrogenase activity.

1 L reactors were used for the fermentation. The pH probes were calibrated by means of a two-point calibration using standard solutions of pH 4.0 and pH 7.0. The reactors were filled with 300 ml of drinking water and autoclaved for 20 min at 121° C. to guarantee sterility. Subsequently, the pO2 probes were polarized overnight (at least for 6 h) on the DASGIP system. On the next morning, the water under the clean bench was removed and replaced by 300 ml of high cell density medium containing 100 mg/l of ampicillin. Subsequently, the pO2 probes were calibrated using a one-point calibration (stirrer: 400 rpm/gassing: 10 sl/h of air) and the feed, correcting means and inducing agent tracks were cleaned by means of Clean-in-Place. For this, the tubing was rinsed with 70% ethanol, subsequently with 1 M NaOH, then with sterile completely demineralized water and lastly filled with the respective media.

The *E. coli* strains producing ALA and ALAME were first grown overnight at 37° C. and 200 rpm for about 18 h from the respective cryocultures in LB medium (25 ml in a 100 ml baffled flask) with 100 mg/l of ampicillin. Subsequently, each 2 ml of the cultures were re-inoculated with 100 mg/l of ampicillin in high cell density medium (glucose 15 g/l (30 ml/l of a separately autoclaved 500 g/l stock solution containing 1% MgSO4.7H2O and 2.2% NH4Cl), (NH4)2SO4 1.76 g/l, K2HPO4 19.08 g/l, KH2PO4 12.5 g/l, yeast extract 6.66 g/l, trisodium citrate dihydrate 2.24 g/l, ammonium iron citrate solution 17 ml/l of a separately autoclaved 1% strength stock solution, trace element solution 5 ml/l separately autoclaved stock solution (HCl (37%) 36.50 g/l, MnCl2.4H2O 1.91 g/l, ZnSO4.7H2O 1.87 g/l, ethylenediaminetetraacetic acid dihydrate 0.84 g/l, H3BO3 0.30 g/l, Na2MoO4.2H2O 0.25 g/l, CaCl2.2H2O 4.70 g/l, FeSO4.7H2O 17.80 g/l, CuCl2.2H2O 0.15 g/l)) (25 ml of each strain in a 100 ml baffled flask) and incubated at 37° C./200 rpm for a further 5.5 h.

The optical density of the cultures at 600 nm was determined in the W3110 ☐FadE [alkB-alaD-TA] as 6.9 and in the W3110 [alkB-alaD-TA] as 7.4. To inoculate the reactors with an optical density of 0.1, each 4.0 ml or 4.4 ml (ΔFadE) were drawn into a 5 ml syringe (under sterile conditions) and the reactors were inoculated by means of a cannula via a septum covered with a layer of 70% ethanol.

The following standard program was used:

| DO regulator | | pH regulator | |
|---|---|---|---|
| Preset | 0% | Preset | 0 ml/h |
| P | 0.1 | P | 5 |
| Ti | 300 s | Ti | 200 s |
| Min | 0% | Min | 0 ml/h |
| Max | 100% | Max | 40 ml/h |

| N (Rotation) | from | to | XO2 (gas mixture) | from | to | F (gas flow) | from | to |
|---|---|---|---|---|---|---|---|---|
| Growth and biotransformation | 0% 400 rpm | 30% 1500 rpm | Growth and biotransformation | 0% 21% | 100% 21% | Growth and biotransformation | 15% 6 sl/h | 80% 72 sl/h |

| Script | |
|---|---|
| Trigger sharp | 31% DO (1/60 h) |
| Induction IPTG | 2 h after feed start |
| Feed trigger | 50% DO |
| Feed rate | 3 [ml/h] |

The experiment carried out can be divided into two phases, the growth at which the cells should achieve a certain optical density, and the following biotransformation, in which after addition of the substrate lauric acid methyl ester a conversion to aminolauric acid ester from enzymes formed in the expression took place. The pH values were controlled unilaterally at pH 6.8 using ammonia (12.5%). During growth and biotransformation, the dissolved oxygen (DO, dissolved oxygen) in the culture was controlled at 30% by means of the stirrer speed and aeration rate. The fermentation was carried out as a fed-batch, the feed start, 5 g/1 h of glucose feed (500 g/l of glucose containing 1% MgSO4.7H2O and 2.2% NH4Cl), being triggered by means of a DO peak. With the feed start, the temperature was also lowered from previously 37° C. to 30° C. The expression of the transaminase was induced 2 h after the feed start by the automatic addition of IPTG (1 mM). The induction of the alk genes took place by the manual addition of DCPK (0.025% v/v) 10 h after the feed start. Before the start of the biotransformation, the optical density of the culture broths was determined.

The start of the biotransformation phase took place 14 h after the feed start. For this, 150 ml of a mixture of lauric acid methyl ester and the ion exchanger oleic acid (tech. 90%) were added to the fermentation broth as a batch. To make available an amino group donor for the transaminase, half an hour before the biotransformation start 5 ml of a 3M ammonium sulphate solution was added to the fermentation broth. For sampling, 2 ml of fermentation broth were removed from the vessel and a part thereof was diluted 1/20 in an acetone/HCl mixture (c(HCl)=0.1 mol/l) and extracted. Samples were taken from all reactors at 1 h, 2 h, 3 h, 4 h, 5 h, 7.5 h, 10.5 h, 19.5 h and 21 h after the start of the biotransformation. The turnover rates for oxygen (OTR=oxygen transfer rate) and carbon (CTR=carbon transfer rate) were determined on the DASGIP systems during the fermentation by means of the waste gas analysis. The fermentation was ended 21 h after the start of the biotransformation. The stirrer, the aeration, the temperature regulation and pH regulation were switched off and the vessel was allowed to stand quietly for 5-10 minutes.

Results:

During the biotransformation phase, in the case of the W3110 Δ FadE [alkB-alaD-TA] with comparable, even slightly increased formation of the product ALAME, a lower oxygen consumption than with W3110 [alkB-alaD-TA] was seen (see FIGS. 3 and 4).

After 10 minutes, in the vessel containing the strain W3110 Δ FadE [alkB-alaD-TA] a marked phase separation in the ratio about 40% upper phase, about 60% lower phase was observed. Between the two phases, there was a thin layer interphase. Samples of the lower and upper phase were filled into a 15 ml Falcon tube and centrifuged at 5500×g for 10 minutes. After this, it appeared that in the tube containing the lower phase aqueous phase and biomass were present to about 95%. In the tube containing the upper phase, it was to be discerned that the upper phase consisted of over 60% organic fraction. In the vessel containing the strain W3110 [alkB-alaD-TA] a homogeneous emulsion was present after 10 minutes and even after a further 20 minutes waiting time no phase separation was seen.

Example 2

Acceleration of the separation of an aqueous from a hydrophobic phase using a Δ FadL mutant as well as a Δ Fade Δ FadL mutant in the biotechnological production of aminolauric acid methyl ester Analogously to Example 1, further experiments using the strains W3110 ΔfadL [alkB-alaD-TA] and
W3110 ΔfadE ΔfadL [alkB-alaD-TA] as well as
W3110 ΔfadE [alkB-alaD-TA] and
W3110 [alkB-alaD-TA]
were carried out as controls.

Again, the DASGIP 8-fold parallel fermentation system was used with exactly the same protocol and parameters as described in Example 1.

After the start of the biotransformation by addition of the lauric acid methyl ester/oleic acid mixture, samples were taken after 1.25, 2.5, 3.5, 20.5, 22.5 and 23.5 hours and worked up according to the abovementioned process. The results are summarized in FIGS. 5, 6 and 7.

After 24 hours, the biotransformations were terminated, pH, temperature and DO regulation were ended and the reactors were allowed to stand quietly for 5-10 minutes.

As in the abovementioned experiment, here too it was possible after a short time to observe a clear separation of the aqueous from the organic phase, provided at least one of the Fad genes was switched off. In the case of the wild-type used as a biocatalyst, i.e. without deletion of one of the Fad genes, no phase separation at all can be discerned (see FIG. 7).

It was likewise seen that in the strains having at least one Fad deletion the oxygen consumption is reduced compared to the wild-type (FIG. 6a).

Numerous modifications and variations on the present invention are possible in light of the above teachings. It is therefore to be understood that within the scope of the appended claims, the invention may be practiced otherwise than as specifically described herein.

REFERENCES

WO 2009/077461: Recombinant cells producing β-aminocarboxylic acids or their lactams
Sangster, Octanol-Water Partition Coefficients: Fundamentals and Physical Chemistry, Vol. 2 of Wiley Series in Solution Chemistry, John Wiley & Sons, Chichester, 1997
F M Ausubel (1995), Current Protocols in Molecular Biology. John Wiley & Sons, Inc.
A M Lesk (2008), Introduction to Bioinformatics, 3rd Edition
Y Fujita, H Matsuoka, and K Hirooka (2007) Mol. Microbiology. 66(4), 829-839
P N Black (1991) J. Bacteriol. 173, 435-442
P N Black, C C DiRusso, A K Metzger, and T L Heimert (1992) J. Biol. Chem. 267, 25513-25520
J. W. Campbell & J E Cronan (200) J. Bacteriol. 184, 3759-3764
A Cornish-Bowden (1995), Fundamentals of Enzyme Kinetics, Portland Press Limited, 1995
S Lobo, G Florova, and K A Reynolds (2001) Biochemistry 40 (39), 11955-64
X Yu, T Liu, F Zhu, and C Khosla (2011) PNAS, electronic publication before printing
K Kameda & W D Nunn (1981) J. Biol. Chem. 256, 5702-5707
Hi Marrakchi, W E DeWolf, C Quinn, J West, B J Polizzi, C Y So et al. (2003) Biochem. J. 370, 1055-1062

Sambrook/Fritsch/Maniatis (1989): Molecular Cloning: A Laboratory Manual, Cold Spring Harbor Laboratory Press, 2nd edition Fuchs/Schlegel (2007) Allgemeine Mikrobiologie, 2008, Georg Thieme Verlag B A Moffatt, and F W Studier (1986) J. Mol. Biol. 189, 113-130

A H Rosenberg, B N Lade, D Chui, S Lin, J J Dunn, and F W Studier (1987) Gene 56, 125-135

F W Studier, A H Rosenberg, J J Dunn, and J W Dubendorff (1990) Meth. Enzymol. 185, 60-89

C Grant, J M Woodley, F Baganz (2011) Enzyme and Microbial Technology, 480-486

D J Koch, M M Chen, J B van Beilen, and F H Arnold (2009) Appl. and Env. Microbiology, 337-344

T Tuschl (2001) ChemBioChem 2: 239-145

The invention claimed is:

1. An enzymatic two-phase system process, comprising:
   preparing an aqueous culture medium of a metabolically active cell having a decreased activity;
   contacting the aqueous culture medium with a hydrophobic organic solution comprising a substrate for biotransformation;
   conducting a biotransformation of the substrate; and
   separating the hydrophobic organic solution comprising a biotransformed substrate from the aqueous culture medium;
   wherein
   the decreased activity of the metabolically active cell is in comparison to a wild-type of the active cell,
   the decreased activity is of at least of one enzyme that catalyses one reaction of β-oxidation of fatty acids, and
   the metabolically active cell comprises a recombinant alkane hydroxylase of alkB type.

2. The process according to claim 1, wherein the at least one enzyme having decreased activity is selected from the group consisting of FadA, FadB, FadD, FadE, and FadL, and variants thereof.

3. The process according to claim 1, wherein the hydrophobic organic solution comprises at least one solvent which is liquid at room temperature, and which is selected from the group consisting of a substituted alkane, an unsubstituted alkane, a cycloalkane, a cycloalkene, an aryl, a fatty acid, a fatty acid ester, an alcohol, a heterocycloalkane, a heterocycloalkene, and a heteroaryl.

4. The process according to claim 3, wherein the organic solution further comprises a fatty acid having more than 12 carbon atoms or an ester thereof.

5. The process according to claim 4, wherein the organic solution comprises a fatty acid and the fatty acid is oleic acid or erucic acid, or the organic solution comprises an ester and the ester is lauric acid methyl ester.

6. The process according to claim 1, wherein the metabolically active cell further comprises a transaminase.

7. The process according to claim 1, wherein the metabolically active cell is a lower eukaryotic cell or a prokaryotic cell.

8. The process according to claim 1, wherein a content the hydrophobic organic solution relative to a total volume of hydrophobic organic solution and aqueous culture medium is at least 5 percent of the total volume.

9. The process according to claim 1, wherein a pH of the aqueous culture medium at a time of contacting the hydrophobic organic solution is from 5 to 9.

10. The process according to claim 1, wherein the metabolically active cell is *E. coli*.

11. The process according to claim 1, wherein the recombinant alkane hydroxylase of alkB type has a sequence homology of at least 75% to the sequence of AlkB of *Pseudomonas putida* Gop1 of database code: CAB54050.1.

12. The process according to claim 1, wherein the recombinant alkane hydroxylase of alkB type has a sequence homology of at least 90% to the sequence of AlkB of *Pseudomonas putida* Gop1 of database code: CAB54050.1.

13. The process according to claim 1, wherein the recombinant alkane hydroxylase of alkB type has a sequence homology of at least 99% to the sequence of AlkB of *Pseudomonas putida* Gop1 of database code: CAB54050.1.

* * * * *